United States Patent [19]
Sakata

[11] Patent Number: 5,198,469
[45] Date of Patent: Mar. 30, 1993

[54] BATH LOTION AND BODY LOTION WITH PHARMACEUTICAL EFFECT

[76] Inventor: Shigenobu Sakata, 3-19-102 Shinkanaoka-cho 1-Chome, Sakai-shi, Osaka, Japan

[21] Appl. No.: 712,814

[22] Filed: Jun. 10, 1991

[30] Foreign Application Priority Data

Dec. 11, 1990 [JP] Japan .................................. 2-410194

[51] Int. Cl.⁵ ........................ A61K 7/48; C07G 17/00; C12P 19/04
[52] U.S. Cl. .................................... 514/777; 435/101; 435/104; 536/114; 514/846; 514/859; 514/861
[58] Field of Search ............... 536/114; 514/846, 861, 514/859; 435/101, 104

[56] References Cited

U.S. PATENT DOCUMENTS

| | | | |
|---|---|---|---|
| Re. 28,781 | 4/1976 | Konig et al. | 514/777 |
| 4,305,961 | 12/1981 | Tsutsumi et al. | 514/777 |
| 4,394,447 | 7/1983 | Cadmus et al. | 435/101 |
| 4,515,700 | 5/1985 | Hitzman | 536/114 |

*Primary Examiner*—Dale R. Ore
*Attorney, Agent, or Firm*—Armstrong, Westerman, Hattori, McLeland & Naughton

[57] ABSTRACT

Disclosed are a bath lotion and a body lotion both consisting essentially of a fermented liquid of high polymer complex polysaccharides. The fermented liquid is obtained by activating and heat-treating a xanthane gum with microorganisms for carbohydrate fermentation. The bath lotion and body lotion are effective and advantageous to health and have a pharmaceutical effect.

2 Claims, No Drawings

BATH LOTION AND BODY LOTION WITH PHARMACEUTICAL EFFECT

FIELD OF THE INVENTION

The present invention relates to a bath lotion and a body lotion which are effective and advantageous to health and which have a pharmaceutical effect.

PRIOR ART

Conventional bath lotions and body lotions are generally prepared from raw materials of surfactants and are used for the purpose of cleaning dirt of the skin and others.

However, such conventional bath lotions and body lotions have a drawback of causing skin irritations or skin rashes though they have a cleaning effect of removing dirt from the skin.

In consideration of the above-mentioned matters, the present invention provides a bath lotion and a body lotion, which are free from the drawback of the surfactant-containing conventional bath lotions and body lotions of causing skin irritations or skin rashes and which have the intrinsic effect of themselves of protecting and activating the skin and additionally have a pharmaceutical effect such as an anti-inflammatory effect or the like.

SUMMARY OF THE INVENTION

In order to attain the above-mentioned object, there is provided in accordance with the present invention a bath lotion and a body lotion which contain, as an essential component, a fermented liquid of high polymer complex polysaccharides as prepared by batch-wise activation and heat treatment of a xanthane gum of a raw material in the presence of microorganisms for carbohydrate fermentation.

DETAILED EXPLANATION OF THE INVENTION

The high polymer complex polysaccharides to be in the bath lotion and body lotion of the present invention have heretofore been utilized widely in various fields as food additives to, for example, ice cream, jelly or the like, and therefore they are harmless to human bodies. In accordance with the present invention, such high polymer complex polysaccharides are used in preparing a bath lotion and a body lotion. Accordingly, the bath lotion and body lotion of the present invention is free from the drawback of the surfactant-containing conventional bath lotions and body lotions of causing skin irritations or skin rashes. The high polymer complex polysaccharides to be used in the present invention are components in a xanthane gum to be obtained by carbohydrate fermentation of vegetables, such as cabbages, carrots, burdocks or the like, in the presence of microorganisms (Xanthomanas compestris), and these are acidic complex polysaccharides containing glucose, mannose, glucone and others. As such a xanthane gum, a powdery product is available, which is a known chemical substance of a commercial product No. 8-535. In the present invention, the substance is batch-wise activated and heated with microorganisms (Xanthomanas compestris) for carbohydrate fermentation to give a fermented liquid of activated acidic high polymer complex polysaccharides, and the fermented liquid is used as a bath lotion and a body lotion.

As mentioned above, the present invention provides a bath lotion and a body lotion which contain, as an active ingredient, a fermented liquid of acidic high polymer complex polysaccharides to be obtained from a raw material of a xanthane gum. Accordingly, the bath lotion and body lotion of the present invention have a function of cleaning dirt of the skin because of the action of the acidic high polymer complex polysaccharides and additionally have another function of elevating the skin-moisturizing effect to thereby refresh and activate the skin as the high polymer complex polysaccharides are absorbed from the skin. Moreover, since the high polymer complex polysaccharides have a bactericidal activity, the bath lotion and body lotion of the present invention containing them have still another effect of curing skin irritations and skin diseases such as acne, prickly heat or various atopic dermatitis to thereby activate the skin.

Specifically, the bath lotion and body lotion of the present invention contains a fermented liquid of high polymer complex polysaccharides, which are widely used as food additives and which are harmless to human bodies, are free from the drawback of the surfactant-containing conventional bath lotions and body lotions of causing skin irritations or skin rashes, and they may protect and activate the skin and have an additional pharmaceutical effect of exterminating the germs of various skin diseases to thereby cure acne, prickly heat and other various atopic dermatitis. Moreover, the bath lotion of the present invention has still another effect of removing the offensive odor of a bath tub or in a bath room and of preventing propagation of dark mold, and it is useful as a bactericide and a fungicide.

EXAMPLES

The present invention will be explained with reference to the following examples.

From 3 to 4% by weight of a powdery xanthane gum (known chemical substance, commercial product No. 8-535) was dissolved in an aqueous solution of a carbohydrate compound and heated up to a temperature of 40° C. to 60° C. with stirring, and the solution was subjected to carbohydrate fermentation with microorganisms (Xanthomanas compestris) for 2 days and then cooled to room temperature (about 17° C.). The fermented liquid was filtered to remove crude dusts and impurities therefrom, then sterilized with ultraviolet rays, and again filtered to remove Escherichia coli and the like to finally obtain a 100% microorganisms-fermented liquid of high polymer complex polysaccharides. To 100% by weight of the fermented liquid was added 0.1% by weight of p-hydroxybenzoic acid. After blended, an Escherichia coli-negative aqueous solution consisting essentially of a fermented liquid of high polymer polysaccharides and containing general bacteria in an amount of 30 cells/ml or less was obtained.

The thus obtained aqueous solution, consisting essentially of a fermented liquid of high polymer complex polysaccharides, was used as a bath lotion and 2cc of the bath lotion was added to a bath tub having 200 liters of water. After taking the bath, the skin-moisturizing effect was elevated and the skin was refreshed and activated. In the case, the offensive odor of the bath tub and in the bath room was removed by the action of the bath lotion, and both the bath tub and the bath room were free from propagation of dark mold. Using the bath water containing the bath lotion, clothes were washed. As a result, the washed clothes were all very clean and had no unfavorable moisture odor. The thus cleaned clothes were stored in a clothing cabinet and they were also free from any unfavorable moisture odor.

On the other hand, the above-mentioned aqueous solution was used as a body lotion and applied to the skin with acne or prickly heat, whereupon the acne or prickly heat was cured and the skin was refreshed and activated.

What is claimed is:

1. A bath or body lotion consisting essentially of a fermentation product prepared by dissolving 3–4% by weight of xanthan gum in an aqueous solution of a carbohydrate compound, heating the solution with stirring to a temperature of 40°–60° C., fermenting the solution with *Xanthomonas campestris*, cooling the solution to room temperature, filtering the cooled solution, and sterilizing the filtrate with ultraviolet light.

2. A bath or body lotion consisting essentially of a fermentation product prepared by dissolving 3–4% by weight of xanthan gum in an aqueous solution of a carbohydrate compound, heating the solution with stirring to a temperature of 40°–60° C., fermenting the solution with *Xanthomanas campestris*, cooling the solution to room temperature, filtering the cooled solution, sterilizing the filtrate with ultraviolet light, and adding benzoic acid, salicylic acid, p-hydroxybenzoic acid, p-hydroxybenzoic acid or methyl p-hydrobenzoate to the sterilized solution.

* * * * *